(12) United States Patent
Fliri et al.

(10) Patent No.: US 10,017,529 B2
(45) Date of Patent: Jul. 10, 2018

(54) METFORMIN DERIVATIVES

(71) Applicant: BioPharma Works LLC, Groton, CT (US)

(72) Inventors: Anton F Fliri, Stonington, CT (US); Robert A Volkmann, Mystic, CT (US)

(73) Assignee: BioPharma Works LLC, Groton, CT (US)

( * ) Notice: Subject to any disclaimer, the term of this patent is extended or adjusted under 35 U.S.C. 154(b) by 0 days.

(21) Appl. No.: 15/511,902

(22) PCT Filed: Sep. 16, 2015

(86) PCT No.: PCT/US2015/050442
§ 371 (c)(1),
(2) Date: Mar. 16, 2017

(87) PCT Pub. No.: WO2016/044433
PCT Pub. Date: Mar. 24, 2016

(65) Prior Publication Data
US 2017/0247400 A1    Aug. 31, 2017

Related U.S. Application Data

(60) Provisional application No. 62/050,987, filed on Sep. 16, 2014.

(51) Int. Cl.
*C07C 381/00* (2006.01)
*C07F 9/6574* (2006.01)
*C07F 9/141* (2006.01)
*C07D 319/06* (2006.01)

(52) U.S. Cl.
CPC ........ *C07F 9/65742* (2013.01); *C07C 381/00* (2013.01); *C07D 319/06* (2013.01); *C07F 9/1411* (2013.01)

(58) Field of Classification Search
CPC .................................................. C07C 381/00
See application file for complete search history.

(56) References Cited

U.S. PATENT DOCUMENTS

2011/0257432 A1    10/2011    DiMauro

FOREIGN PATENT DOCUMENTS

WO    03032908 A2    4/2003
WO    2010100337 A1    9/2010

OTHER PUBLICATIONS

Huttunen et al. "Convenient microwave-assisted synthesis of lipophilic sulfenamide prodrugs of metformin." Euorpean Journal of Pharmaceutical Sciences, vol. 49, No. 4, Jun. 1, 2013, ISSN: 0928-0987, DOI: 10.1016/J. EJPS.2013.05.023, 6 pages.
International Search Report and Written Opinion, Application No. PCT/US2015/050442, dated May 4, 2016, 16 pages.

*Primary Examiner* — Paul V Ward
(74) *Attorney, Agent, or Firm* — Ziegler IP Law Group, LLC

(57) ABSTRACT

The present invention relates to novel biguanide derivatives including their pharmaceutically acceptable salts. The invention also relates processes for the preparation of, intermediates used in the preparation of, pharmaceutical compositions containing and the uses of such compounds in treating disorders such as diabetes.

19 Claims, No Drawings

METFORMIN DERIVATIVES

This application is the National Stage of International Application No. PCT/US2015/050442, filed Sep. 16, 2015, which claims the benefit of U.S. Provisional Application No. 62/050,987, filed Sep. 16, 2014.

FIELD OF INVENTION

The present invention relates to novel biguanide derivatives including their pharmaceutically acceptable salts. The invention also relates processes for the preparation of, intermediates used in the preparation of, pharmaceutical compositions containing and the uses of such compounds in treating disorders such as diabetes.

BACKGROUND OF THE INVENTION

Metformin is an antihyperglycemic agent of the biguanide class used in the treatment of non-insulin dependent diabetes mellitus (NIDDM) as well as other disorders. It is marketed as immediate release formulations in the form of its hydrochloride salt (such as Glucophage) and so-called extended release formulations (Fortamet, Glucophage XR, and Glumetza).

Metformin hydrochloride has intrinsically poor permeability in the lower portion of the gastrointestinal tract leading to absorption almost exclusively in the upper part of the gastrointestinal tract. Its oral bioavailability is in the range of 40 to 60% decreasing with increasing dosage which suggests some kind of saturable absorption process, or permeability/transit time limited absorption. It also has a very high water solubility (>300 mg/ml at 25° C.). This can lead to difficulty in providing a slow release rate from a formulation and problems in controlling the initial burst of drug from such a formulation. These two difficulties are further compounded by the high unit dose, 500 mg per tablet, usually required for metformin hydrochloride.

Extended release dosage forms that release metformin at a rate likely to provide the desired plasma levels of drug for an extended time period have been introduced in an attempt to maintain or even improve bioavailability. These formulations have had mixed results in the clinical setting.

New metformin modalities have been reported including certain sulfenylguanidine prodrugs of metformin referred to in International Patent Publication WO 2010/100337, published Sep. 10, 2010. International Patent Publication WO 2004/004774, published Jan. 15, 2004, refers to compositions of panthetine for the treatment of dyslipidemia. United States Patent Publication 2011/0257432, published Oct. 20, 2011 refers to certain metformin-cysteine prodrugs.

There still remains a great need for new metformin type compounds that have greater bioavailability, pharmacology and ease of use.

SUMMARY OF THE INVENTION

The present invention relates to novel compounds of Formula

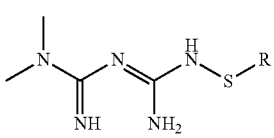

I wherein R is

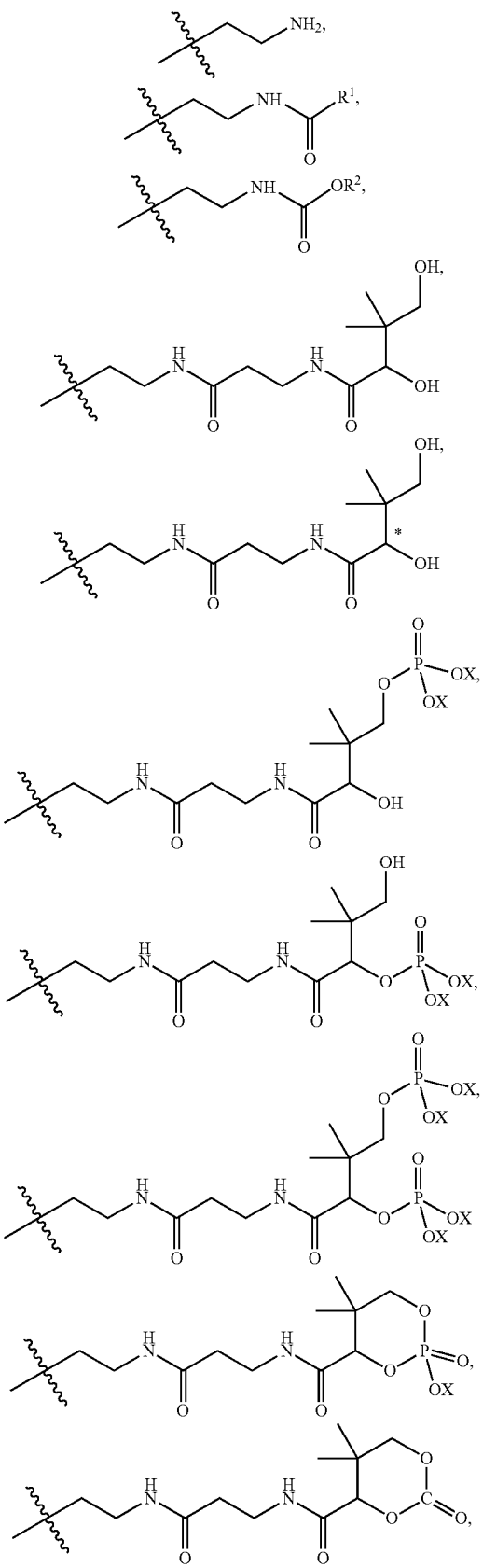

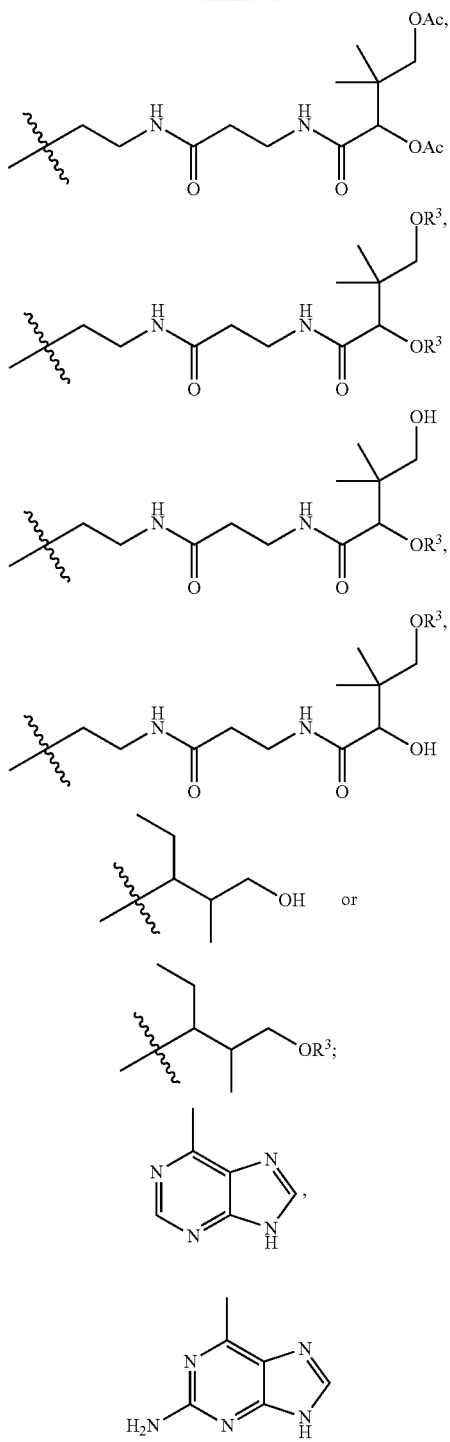

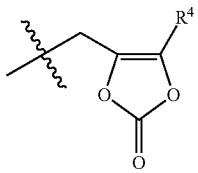

$R^4$ is H, alkyl, cycloalkyl, $CO_2R^1$ $R^5$ is alkyl, functionalized alkyl, cycloalkyl, aryl, or heteroaryl;

$R^6$ is H or $R^5$; and

X is H, $Na^+$, $K^+$, $Ca^{2+}$, $Mg^{2+}$, $^+NH_3CH_2CH_2OH$, $^+N(R^2)_4$, $^+NH_4$

As used herein, the term "alkyl" is defined to include saturated or unsaturated hydrocarbons including straight chains and branched chains and 1 to 20 carbon atoms. For example, as used herein, the term alkyl refers to linear or branched radicals of 1 to 6 carbon atoms (e.g., methyl, ethyl, n-propyl, isopropyl, n-butyl, iso-butyl, secondary-butyl, tertiary-butyl), optionally substituted by 1 to 5 suitable substituents. Unsaturated hydrocarbons have at least one carbon-carbon double bond, including straight chains and branched chains and 2 or more carbon atoms. For example, as used herein, the term alkyl includes straight or branched chain unsaturated radicals of 2 to 20 carbon atoms, including, but not limited to ethenyl, 1-propenyl, 2-propenyl (allyl), iso-propenyl, 2-methyl-1-propenyl, 1-butenyl, 2-butenyl, and the like; optionally substituted by 1 to 5 suitable substituents. When the compounds of Formula I contain an alkenyl group, the alkenyl group may exist as the pure E (entgegen) form, the pure Z (zusammen) form, or any mixture thereof. Unsaturated hydrocarbons have at least one carbon-carbon triple bond, including straight chains and branched chains, and 2 to 20 carbon atoms. For example, as used herein, the term alkyl is used herein to include straight or branched hydrocarbon chain unsubstituted (e.g. alkynyl) radical having 2 to 20 carbon atoms and one triple bond; optionally substituted by 1 to 5 suitable substituents.

Functionalized alkyl refers to alkyl groups in which one or more carbon atoms have been replaced with a heteroatom such as —N═, —NH—, N, S and O.

As used herein, the term "cycloalkyl" is defined to include saturated or unsaturated (non aromatic) monocyclic or bicyclic hydrocarbon rings (e.g., cyclopropyl, cyclobutyl, cyclopentyl, cyclohexyl, cycloheptyl, cyclooctyl, cyclononyl); optionally substituted by 1 to 5 suitable substituents. The cycloalkyl group has 3 to 12 carbon atoms. One group of monocyclic cycloalkyl rings have 3 to 6 carbon atoms. In another embodiment the cycloalkyl may optionally contain one, two or more non cumulative non aromatic double or triple bonds. Bicyclic hydrocarbon is defined to include a cycloalkyl as defined above which is bridged to a second carbocyclic ring (e.g., bicyclo[2.2.1]heptanyl, bicyclo[3.2.1]octanyl and bicyclo[5.2.0]nonanyl, etc.). Preferably, the bicycloalkyl group has 6 to 20 carbon atoms. More preferably, the bicycloalkyl group has 6 to 15 carbon atoms. Most preferably, the bicycloalkyl group has 6 to 12 carbon atoms. The bicycloalkyl is optionally substituted by 1 to 5 suitable substituents. In one embodiment the bicycloalkyl may optionally contain one, two or more non cumulative non aromatic double or triple bonds.

As used herein, the term "aryl" is defined to include all-carbon monocyclic or fused-ring polycyclic (i.e., rings which share adjacent pairs of carbon atoms) groups having a completely conjugated pi-electron system. The aryl group $R^1$ is alkyl, functionalized (heteroatom substituted) alkyl, cycloalkyl, aryl, heteroaryl, heterocyclic, carboxylate drug conjugate, fatty acid conjugate, bile acid conjugate, or amino acid conjugate;

$R^2$ is alkyl, cycloalkyl, heterocyclic, aryl $R^3$ is $(C═O)R^2$, $(C═O)H$, $C(R^4)_2O(C═O)R^5$, $C(R^4)_2O(C═O)OR^5$, $C(R^4)_2O(P═O)(OX)_2$, $C(R^4)_2O(C═O)N(R^6)_2$, $C(R^4)_2O$ $(C═O)(CHR^4)NR^6R^4$, or $C(R^4)_2O(C═O)(CHR^6)N(R^6)_2$, has 6, 8, 9, 10 or 12 carbon atoms in the ring(s). In one embodiment the aryl group has 6 or 10 carbon atoms in the ring(s). One aryl group of particular interest is the 6 carbon atom phenyl ring. For example, as used herein, the term "aryl" means aromatic radicals containing from 6 to 10 carbon atoms such as phenyl, naphthyl, tetrahydronaphthyl, anthracenyl, indanyl and the like. The aryl group is optionally substituted by 1 to 5 suitable substituents.

As used herein, the term "heteroaryl" is defined to include monocyclic or fused-ring polycyclic aromatic heterocyclic groups with one or more heteroatoms selected from O, S and N in the ring. The heteroaryl group has 5 to 12 ring atoms including one to five heteroatoms selected from O, S, and N. For example, as used herein, the term "5 to 12 membered heteroaryl" means aromatic radicals containing at least one ring heteroatom selected from O, S and N and from 1 to 11 carbon atoms such as pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like. The heteroaryl group is optionally substituted by 1 to 5 suitable substituents.

As used herein, the term "heterocyclic" is defined to include a monocyclic, bridged, polycyclic or fused polycyclic saturated or unsaturated non-aromatic 3 to 13 membered ring including 1 or more heteroatoms selected from O, S and N. Examples of such heterocycloalkyl rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl, and the like. Further examples of said heterocycloalkyl rings are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, 1,2-tetrahydrothiazin-2-yl, 1,3-tetrahydrothiazin-3-yl, 1,2-tetrahydrodiazin-2-yl, 1,3-tetrahydrodiazin-1-yl, 1,4-oxazin-2-yl, 1,2,5-oxathiazin-4-yl and the like. The heterocycloalkyl ring is optionally substituted by 1 to 5 suitable substituents.

"Ac" as used herein refers to the acetyl group, $CH_3(C=O)$.

Bile Acids refers to steroid acid conjugate derivatives of cholic acid including Cholic acid, Chenodeoxycholic acid, Glycocholic acid, Taurocholic acid, Deoxycholic acid, Lithocholic acid including glycine or taurine amino acid conjugates.

Fatty Acid refers to a carboxylic acid conjugate with a long aliphatic tail (chain), which may be either saturated or unsaturated. Most naturally occurring fatty acids have a chain of an even number, 4 to 28, of carbon atoms. Fatty Acids include Lipoic acid, Myristoleic acid, Palmitoleic acid, Sapienic acid, Oleic acid, Elaidic acid, Vaccenic acid, Linoleic acid, Linoelaidic acid, α-Linolenic acid, Arachidonic acid, Eicosapentaenoic acid, Erucic acid, Docosahexaenoic acid, Caprylic acid, Capric acid, Lauric acid, Myristic acid, Palmitic acid, Stearic acid, Arachidic acid, Behenic acid, Lignoceric acid, and Cerotic acid.

Amino Acid conjugate as used herein refers to an $R^1$ side chain that taken together with the adjacent NH—(C=O) moiety forms an amino acid selected from the group consisting of Alanine, Arginine, Asparagine, Aspartic acid, Cysteine, Glutamic acid, Glutamine, Glycine, Ornithine, Proline, Selenocysteine, Serine, Tyrosine, Histidine, Isoleucine, Leucine, Lysine, Methionine, Phenylalanine, Threonine, Tryptophan, and Valine.

Carboxylate Drug Conjugate refers to active pharmaceutical agents containing a carboxylic acid functional group that may be derivatized with the $R^1(C=O)$ moiety to form a drug conjugate with the molecule of Formula I. Carboxylate drug conjugates include aconiazide, adapalene, ambrisentan, aminolevulinic acid, anthranilic acid, balsalazide, bentiromide, benzoic acid, (benzylsulfonamido)benzoic acid, betaine, bromfenac, capric acid, carbenicillin, carnitine, levocarnitine, carprofen, chloramphenicol, clorazepate, clorazepic acid, cloxacillin, digalloyl trioleate, disofenin, gallic acid, g-aminobutyric acid, piperidic acid, gamma-aminobutyric acid, aminobutyricacid(gaba), grepafloxacin, halazone, hetacillin, iodoalphionic acid, iodohippurate, ketoprofen, dexketoprofen, s (+) ketoprofen, lidofenin, alpha lipoic acid, thioctic acid, lodoxamide, lomefloxacin, malic acid, mebrofenin, meclofenamic acid, mefenamic acid, mesalamine, methallenestril, methotrexate, methyldopa, metyrosine, racemetirosine, nalidixic acid, nateglinide, nedocromil, nicotinic acid, niacin, norfloxacin, orotic acid, oxaprozin, oxolinic acid, ozolinone, paraaminobenzoic acid, aminobenzoic acid, phenoxyacetic acid, phenylbutyrate, phthalylsulfamethizole, phthalylsulfathiazole, probenecid, succinic acid, succinylsulfathiazole, sulfasalazine, temafloxacin, I-threonine, ticrynafen, tiopronin, dextiopronin, tolmetin, tranexamic acid, undecylenate, valproic acid, vigabatrin, and zomepirac.

As used herein the term "Formula I" is defined to include all forms of the compound of Formula I, including hydrates, solvates, isomers, crystalline and non-crystalline forms, isomorphs, and polymorphs thereof.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3$$^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970).

Hereinafter all references to compounds of formula I include references to salts, solvates, multi-component complexes and liquid crystals thereof and to solvates, multi-component complexes and liquid crystals of salts thereof.

The compounds of the invention include compounds of Formula I as hereinbefore defined, including all polymorphs and crystal habits thereof, isomers thereof (including optical, geometric and tautomeric isomers) as hereinafter defined and isotopically-labeled compounds of Formula I.

The compounds of Formula I may have asymmetric carbon atoms and may exist as two or more stereoisomers. The carbon-carbon bonds of the compounds of Formula I may be depicted herein using a solid line (—), a solid wedge (⬛), or a dotted wedge (⋯). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present. Stereoisomers of Formula I include cis and trans isomers, optical isomers such as R and S enantiomers, diastereomers, geometric isomers, rotational isomers, conformational isomers, and tautomers of the compounds of Formula I, including compounds exhibiting more than one type of isomerism; and mixtures thereof (such as racemates and diastereomeric pairs). Also included are acid addition or base addition salts wherein the counterion is optically active, for example, d-lactate or l-lysine, or racemic, for example, dl-tartrate or dl-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the Formula I may exhibit the phenomena of tautomerism and structural isomerism. For example, the compounds of Formula I may exist in several tautomeric forms, including the enol and imine form, and the keto and enamine form and geometric isomers and mixtures thereof. All such tautomeric forms are included within the scope of compounds of Formula I. Tautomers exist as mixtures of a tautomeric set in solution. In solid form, usually one tautomer predominates. Even though one tautomer may be described, the present invention includes all tautomers of the compounds of Formula I.

The present invention includes all pharmaceutically acceptable isotopically-labelled compounds of formula I wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula I, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula I can generally be prepared by conventional techniques known to those skilled in the art or by processes analogous to those described in the accompanying Examples and Preparations using an appropriate isotopically-labeled reagent in place of the non-labeled reagent previously employed.

An embodiment of the present invention relates to a compound of Formula I, wherein R is

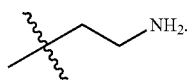 [SMILES: *CCN]

Another embodiment of the present invention relates to a compound of Formula I, wherein R is

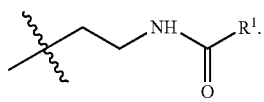

Another embodiment of the present invention relates to a compound of Formula I, wherein R is

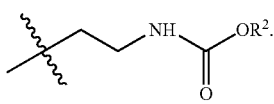

Another embodiment of the present invention relates to a compound of Formula I, wherein R is

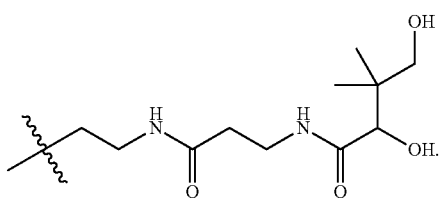 [SMILES: *CCNC(=O)CCNC(=O)C(O)C(C)(C)CO]

Another embodiment of the present invention relates to a compound of Formula I, wherein R is

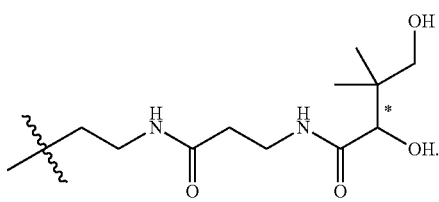 [SMILES: *CCNC(=O)CCNC(=O)C(O)C(C)(C)CO]

Another embodiment of the present invention relates to a compound of Formula I, wherein R is

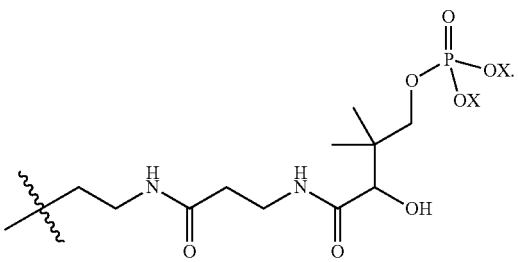

Another embodiment of the present invention relates to a compound of Formula I, wherein R is

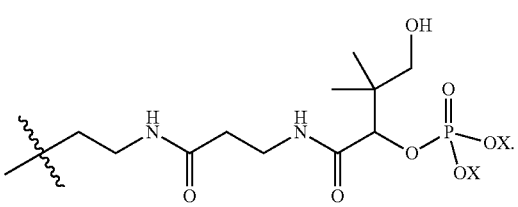

Another embodiment of the present invention relates to a compound of Formula I, wherein R is

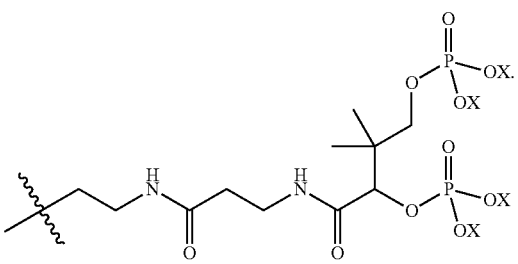

Another embodiment of the present invention relates to a compound of Formula I, wherein R is

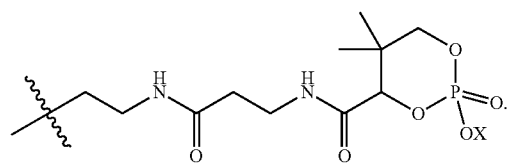

Another embodiment of the present invention relates to a compound of Formula I, wherein R is

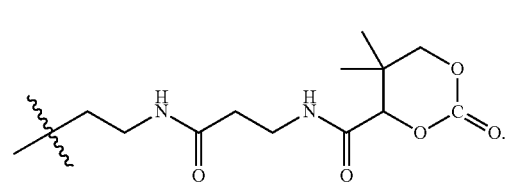 [SMILES: *CCNC(=O)CCNC(=O)C1OC(=O)OCC1(C)C]

Another embodiment of the present invention relates to a compound of Formula I, wherein R is

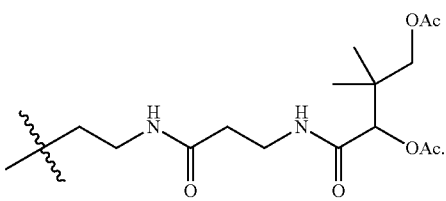 [SMILES: *CCNC(=O)CCNC(=O)C(OC(C)=O)C(C)(C)COC(C)=O]

Another embodiment of the present invention relates to a compound of Formula I, wherein R is

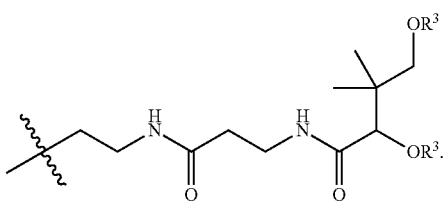

Another embodiment of the present invention relates to a compound of Formula I, wherein R is

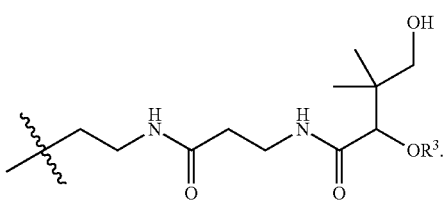

Another embodiment of the present invention relates to a compound of Formula I, wherein R is

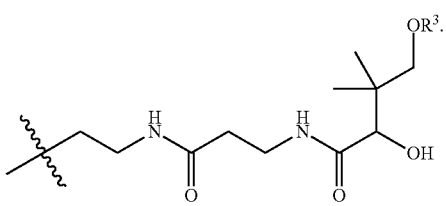

Another embodiment of the present invention relates to a compound of Formula I, wherein R is

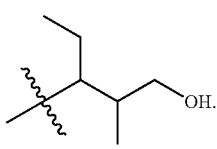 [SMILES: *C(CC)C(C)CO]

Another embodiment of the present invention relates to a compound of Formula I, wherein R is

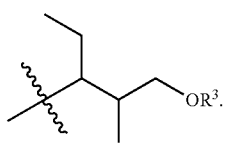

Another embodiment of the present invention relates to a compound of Formula I, wherein R is as defined above and $R^1$ is alkyl.

Another embodiment of the present invention relates to a compound of Formula I, wherein R is as defined above and $R^1$ is linear alkyl of one to 20 carbon atoms.

Another embodiment of the present invention relates to a compound of Formula I, wherein R is as defined above and $R^1$ is aryl.

Another embodiment of the present invention relates to a compound of Formula I, wherein R is as defined above and $R^1$ is cycloalkyl.

Another embodiment of the present invention relates to a compound of Formula I, wherein R is as defined above and $R^1$ is cycloalkyl of 3 to 12 carbon atoms.

Another embodiment of the present invention relates to a compound of Formula I, wherein R is as defined above and $R^1$ is cycloalkyl is selected from the group consisting of cyclopropyl, cyclobutyl, cyclopentyl and cyclohexyl.

Another embodiment of the present invention relates to a compound of Formula I, wherein R is as defined above and $R^1$ is heterocyclic.

Another embodiment of the present invention relates to a compound of Formula I, wherein R is as defined above and $R^1$ is heterocyclic selected from the group consisting of thiopurine and thioguanine.

Another embodiment of the present invention relates to a compound of Formula I, wherein R is as defined above and $R^1$ is heteroaryl.

Another embodiment of the present invention relates to a compound of Formula I, wherein R is as defined above and $R^1$ is heteroaryl selected from the group consisting of pyridyl, pyrazinyl, pyrimidinyl, pyridazinyl, thienyl, furyl, imidazolyl, pyrrolyl, oxazolyl, thiazolyl.

Another embodiment of the present invention relates to a compound of Formula I, wherein R is as defined above and $R^1$ is carboxylate drug conjugate.

Another embodiment of the present invention relates to a compound of Formula I, wherein R is as defined above and $R^1$ is fatty acid conjugate.

Another embodiment of the present invention relates to a compound of Formula I, wherein R is as defined above and $R^1$ is bile acid conjugate.

Another embodiment of the present invention relates to a compound of Formula I, wherein R is as defined above and $R^1$ is amino acid conjugate.

Another embodiment of the present invention relates to a compound of Formula I, wherein R is as defined above, $R^1$ is as defined above and wherein each $R^2$ is independently alkyl.

Another embodiment of the present invention relates to a compound of Formula I, wherein each $R^2$ is aryl.

Another embodiment of the present invention relates to a compound of Formula I, wherein R is as defined above, $R^1$ is as defined above and wherein each $R^3$ is independently (C=O)$R^2$ and each $R^2$ is independently selected from the group consisting of hydrogen, alkyl, aryl, cycloalkyl, heterocyclic and heteroaryl.

Another embodiment of the present invention relates to a compound of Formula I, wherein $R^1$ selected from the group consisting of carboxylate drug conjugate, fatty acid conjugate, bile acid conjugate, or amino acid conjugate.

Another embodiment of the present invention relates to a compound of Formula I, wherein each $R^3$ is independently $C(R^4)_2O(C=O)R^6$.

Another embodiment of the present invention relates to a compound of Formula I, wherein each $R^3$ is independently $C(R^4)_2O(C=O)OR^6$.

Another embodiment of the present invention relates to a compound of Formula I, wherein each $R^3$ is independently $C(R^4)_2O(P=O)(OX)_2$.

Another embodiment of the present invention relates to a compound of Formula I, wherein each $R^3$ is independently $C(R^4)_2O (C=O)N(R^6)_2$.

Another embodiment of the present invention relates to a compound of Formula I, wherein each $R^3$ is independently $C(R^4)_2O (C=O)(CHR^4)NR^6R^4$.

Another embodiment of the present invention relates to a compound of Formula I, wherein each $R^3$ is independently $C(R^4)_2O(C=O)(CHR^6)N(R^6)_2$.

Another embodiment of the present invention relates to a compound of Formula I, wherein each $R^4$ is independently Hydrogen.

Another embodiment of the present invention relates to a compound of Formula I, wherein each $R^5$ is independently alkyl.

Another embodiment of the present invention relates to a compound of Formula I, wherein each $R^5$ is independently cycloalkyl.

Another embodiment of the present invention relates to a compound of Formula I, wherein each $R^5$ is independently arylalkyl.

Another embodiment of the present invention relates to a compound of Formula I, wherein each $R^5$ is independently heteroaryl.

Another embodiment of the present invention relates to a compound of Formula I, wherein $R^6$ is alkyl.

Another embodiment of the present invention relates to a compound of Formula I, wherein $R^6$ is cycloalkyl.

Another embodiment of the present invention relates to a compound of Formula I, wherein $R^6$ is aryl.

Another embodiment of the present invention relates to a compound of Formula I, wherein $R^6$ is heteroaryl.

Another embodiment of the present invention relates to a compound of Formula I, wherein each $R^6$ is independently H.

Another embodiment of the present invention relates to a compound of Formula I, wherein each $R^7$ is independently $R^6$ and $R^6$ is alkyl.

Another embodiment of the present invention relates to a compound of Formula I, wherein each $R^6$ is independently $R^5$ and $R^5$ is cycloalkyl.

Another embodiment of the present invention relates to a compound of Formula I, wherein each $R^6$ is independently $R^5$ and $R^5$ is aryl.

Another embodiment of the present invention relates to a compound of Formula I, wherein each $R^6$ is independently $R^5$ and $R^5$ is heteroaryl.

Another embodiment of the present invention relates to a compound of Formula I, wherein each X is H.

Another embodiment of the present invention relates to a compound of Formula I, wherein each X is Na, K, Ca or Mg.

Another embodiment of the present invention relates to a compound of Formula I, wherein each X is $NH_3CH_2CH_2OH$, or $N(R^2)_4$, $NH_4$.

In another embodiment, the invention also relates to the compounds described as in the Examples section of the subject application, and pharmaceutically acceptable salts thereof. Specific compounds include: N-(3,5-diimino-2-methyl-7-thia-2,4,6-triazanonan-9-yl)acetamide; 3,5-diimino-2,17,17-trimethyl-11,15-dioxo-7-thia-2,4,6,10,14-pentaazaoctadecane-16,18-diyl diacetate; and N-(3,5-diimino-2-methyl-11-oxo-7-thia-2,4,6,10-tetraazatridecan-13-yl)-2,4-dihydroxy-3,3-dimethylbutanamide.

Another embodiment of the invention is directed to a method for treating a disorder selected from the group consisting of diabetes, cancer, neurodegenerative diseases, depression, schizoaffective diseases, non-fatty liver (NAFLD/NASH) disease, Cystinosis, fibrotic diseases, nephropathic cystinosis, radiation damage, malaria, prolactin-secreting adenomas, acetaminophen poisoning, artherosclerosis, alcoholism, vascular disease, hyperlipidaemia, platelet dysfunction, lipid-peroxidation dysfunction, inflammation, skin disorders, elevated levels of interstitial extracellular matrix (ECM) disorders, chronic kidney disease (CKD), interstitial fibrosis, diabetes mellitus and systemic lupus erythematosus in a mammal, preferably a human, comprising administering to said mammal a therapeutically effective amount of a compound of Formula I or pharmaceutically acceptable salt thereof.

The term "therapeutically effective amount" as used herein refers to that amount of the compound being administered which will relieve to some extent one or more of the symptoms of the disorder being treated. In reference to the treatment of diabetes, a therapeutically effective amount refers to that amount which has the effect of improving one or more symptoms of diabetes such as suppressing glucose production by the liver (hepatic gluconeogenesis).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

An embodiment of the invention relates to a method for treating Neurodegenerative diseases such as Parkinson's and Huntington's disease.

Another embodiment of the invention relates to a method for treating depression (such as through enhancing central BDNF levels).

Another embodiment of the invention relates to a method for treating Schizoaffective disease.

Another embodiment of the invention relates to a method for treating Non-fatty liver diseases. Non-alcoholic fatty liver disease (NAFLD) is a fatty liver disease occurring when fat is deposited (steatosis) in the liver not due to excessive alcohol use. Non-alcoholic steatohepatitis (NASH) is an extreme form of NAFLD regarded as a major cause of cirrhosis of the liver of unknown cause.

Another embodiment of the invention relates to a method for treating fibrotic diseases consisting of: atherosclerosis, asthma, cardiac fibrosis, organ transplant fibrosis, colloid and hypertrophic scar, muscle fibrosis, pancreatic fibrosis, bone-marrow fibrosis, liver fibrosis, cirrhosis of liver and gallbladder, scleroderma, pulmonary fibrosis, diffuse parenchymal lung disease, idiopathic interstitial fibrosis, interstitial pneumonitis, desquamative interstitial pneumonia, respiratory bronchiolitis, interstitial lung disease, acute interstitial pneumonitis, nonspecific interstitial pneumonia, cryptogenic organizing pneumonia, lymphocytic interstitial pneumonia, renal fibrosis, or chronic kidney disease.

Another embodiment of the invention relates to a method for treating Nephropathic cystinosis.

Another embodiment of the invention relates to a method for protecting against effects of radiation.

Another embodiment of the invention relates to a method for treating Malaria (particularly in combination with Artemisinine and Dihydroartemisinin).

Another embodiment of the invention relates to a method for treating prolactin-secreting adenomas.

Another embodiment of the invention relates to a method for treating acetaminophen poisoning.

Another embodiment of the invention relates to a method for treating Artherosclerosis. Another embodiment of the invention relates to a method for treating effects of Alcoholism.

Another embodiment of the invention relates to a method for treating vascular diseases.

Another embodiment of the invention relates to a method for treating hyperlipidaemia.

Another embodiment of the invention relates to a method for improving platelet function.

Another embodiment of the invention relates to a method for preventing lipid-peroxidation dysfunction.

Another embodiment of the invention relates to a method for treating inflammation.

Another embodiment of the invention relates to a method for treating skin disorders.

Another embodiment of the invention relates to a method for improving skin condition.

Another embodiment of the invention relates to a method for treating Polycystic ovary syndrome (PCOS), also called hyperandrogenic anovulation, also known as Stein-Leventhal syndrome.

Another embodiment of the invention relates to a method for treating disorder associated with elevated levels of interstitial extracellular matrix (ECM) in a tissue wherein the tissue comprises an organ selected from the group consisting of lung, heart, blood vessel, liver, gallbladder, kidney, skin, lung, muscle, pancreas, and thyroid.

Another embodiment of the invention relates to a method for slowing or halting the progression of chronic kidney disease (CKD), said method comprising administering, to a patient diagnosed with CKD, an effective amount of a compound of Formula I, or a salt thereof; wherein the administration of said compound of Formula I or a salt thereof, results in the slowing or halting of CKD progression in the patient.

Another embodiment of the invention relates to a method for reducing interstitial fibrosis in response to kidney injury, said method comprising administering, to a patient at risk for developing CKD, an effective amount of a compound of Formula I or a salt thereof; wherein the administration of sulfenamide prodrug or a salt thereof, results in the reduction of interstitial fibrosis in the patient Another embodiment of the invention relates to a method for reducing interstitial fibrosis in response to kidney injury, wherein the reduction of interstitial fibrosis is measured by a decrease in ECM accumulation Another embodiment of the invention relates to a method for reducing interstitial fibrosis in response to kidney injury, wherein the patient is diagnosed with diabetes mellitus.

Another embodiment of the invention relates to a method for reducing interstitial fibrosis in response to kidney injury, wherein the patient has suffered kidney trauma.

Another embodiment of the invention relates to a method for reducing interstitial fibrosis in response to kidney injury, wherein the effective amount of the compound of Formula I or a salt thereof is about 1 grams/m$^2$/day to about 3 grams/m$^2$/day.

Administration of the compounds of Formula I may be effected by any method that enables delivery of the compounds to the site of action. These methods include oral routes, intraduodenal routes, parenteral injection (including intravenous, subcutaneous, intramuscular, intravascular or infusion), topical, and rectal administration.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the active agent are well-known in the relevant art and would be understood to be encompassed by the skilled artisan once provided the teachings disclosed herein.

The amount of the compound of Formula I administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The invention is also directed to pharmaceutical compositions comprising a compound of Formula I or a pharmaceutically acceptable salt thereof, and a pharmaceutically acceptable carrier.

The present invention also includes the use of a combination of a compound as provided in Formula I and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I or a pharmaceutically acceptable salt of the compound; (b) a second pharmaceutically active agent; and (c) a pharmaceutically acceptable carrier, vehicle or diluent.

As used herein, the term "combination therapy" refers to the administration of a compound of Formula I together with an at least one additional pharmaceutical or medicinal agent, either sequentially or simultaneously.

Various pharmaceutically active agents may be selected for use in conjunction with the compounds of Formula I, depending on the disease, disorder, or condition to be treated.

The invention also relates to compositions comprising a compound of Formula I or an acceptable salt thereof (e.g., pharmaceutical compositions). Accordingly, in one embodiment, the invention relates to a pharmaceutical composition comprising a compound of Formula I, a pharmaceutically acceptable carrier and, optionally, at least one additional medicinal or pharmaceutical agent. In one embodiment, the at least one additional medicinal or pharmaceutical agent is an anti-diabetic agent as described below.

The pharmaceutical acceptable carrier may comprise any conventional pharmaceutical carrier or excipient. Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulations, solution suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages.

In one preferred embodiment the composition comprises a therapeutically effective amount of a compound of Formula I and a pharmaceutically acceptable carrier.

The compounds of the invention may be used in combination with anti-diabetic agents including insulin secreatagogues such as sulfonylureas (including glimepiride, Glipizide, Glucotrol, and Glyburide), Meglitinides (such as repaglinide (Prandin) and nateglinide (Starlix)), DPP4 inhibitors (including Januvia (sitagliptin), Onglyza (saxagliptin), Tradjenta (linagliptin), and Galvus (vildagliptin)), incretin mimetics such as GLP-1 (including Byetta, Exenatide, Victoza (liraglutide) and Syncria (albiglutide)), amylin mimetics (such as pramlintide (Symlin)) and sensitizers (such as PPAR inhibitors including Avandia (rosiglitazone), ACTOS, and Pioglitazone) and α-glucosidase inhibitors (including Acarbose (Precose) and miglitol (Glyset)).

The compounds of the invention may also be used therapeutically in combination with insulins including Lantus, Apidra, Insuman, Levemer, and Humalog.

The compounds of the present invention can be administered in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrix-metalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

The compounds of the invention may also be used in combination with dyslipidemia agents including bile-acid-binding resins (such as cholestyramine (Questran Light), and colestipol hydrochloride (Colestid)), Statins (including lovastatin (Mevacor), simvastatin (Zocor), pravastatin (Pravachol), fluvastatin (Lescol), rosuvastatin (Crestor) and atorvastatin (Lipitor)), Niacin (nicotinic acid), Niaspan, Nicostatin, Fibrates (such as clofibrate (Atromid), fenofibrate (Tricor) and bezafibrate (Bezalip)) and Ezetimibe (Zetia).

DETAILED DESCRIPTION OF THE INVENTION

Compounds of the Formula I may be prepared according to the following reaction schemes and accompanying discussion. Unless otherwise indicated, R, $R^1$, $R^2$, $R^3$, $R^4$, $R^5$, $R^6$ and X, and structural Formula I, are as defined above in the reaction schemes and discussion that follow. In general the compounds of this invention may be made by processes which include processes analogous to those known in the chemical arts, particularly in light of the description contained herein. Certain processes for the manufacture of the compounds of this invention are provided as further features of the invention and are illustrated by the following reaction schemes. Other processes may be described in the experimental section.

As an initial note, in the preparation of the Formula I compounds it is noted that some of the preparation methods useful for the preparation of the compounds described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, Protective Groups in Organic Synthesis, John Wiley & Sons, New York, 1991. For example, certain compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-t-butoxycarbonyl, benzyloxycarbonyl, and 9-fluorenylmethylenoxycarbonyl for amines and lower alkyl or benzyl esters for carboxylic acids) which are generally not chemically reactive under the reaction conditions described and can typically be removed without chemically altering other functionality in the Formula I compound.

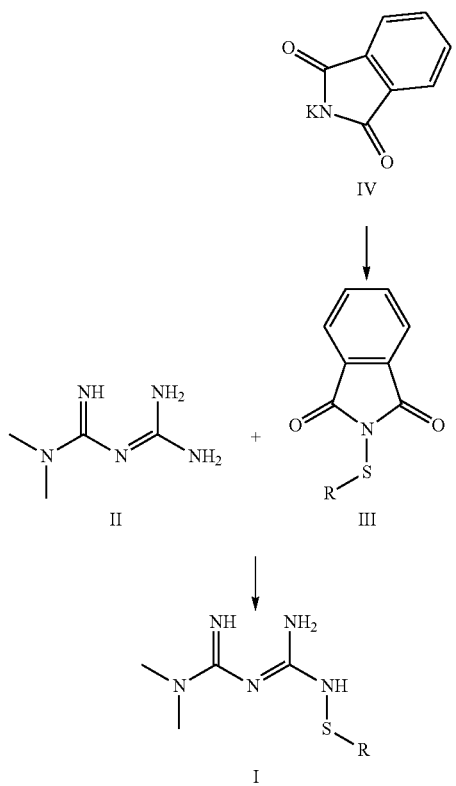

Scheme 1

Scheme 1 illustrates the synthesis of compounds of Formula I. Referring to Scheme 1, a compound of the Formula I may be prepared from a compound of Formula II (i.e. metformin) by reaction with an activated R—S reagent of Formula III. Suitable solvents include polar aprotic solvents such as DMF, DMSO, THF, or acetonitrile. Reactions of the present invention may be conducted within a range of 0° C. to 40° C., for 0.5 hours to 6 hours.

Compounds of Formula III may be prepared from in situ formed bromo-thiols by reaction with a phthalimide of Formula IV. Suitable solvents include DMF, DMSO, THF, methylene chloride, acetone, ethyl acetate or acetonitrile. These reactions may include a catalyst such as pyridine, lutidine or DINAP. Reactions of the present invention may be conducted within a range of 0° C. to 40° C., for 1 hour to 24 hours.

Bromothiols may be prepared from methods well known to those skilled in the art such as from disulfanyl alkylamides by bromination with a reagent such as $Br_2$ or N-bromosuccinimide. Disulfanyl alkylamides are also commercially available.

Compounds of Formula I that have chiral centers may exist as stereoisomers, such as racemates, enantiomers, or diastereomers. Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of Formula I (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomeric conglomerates may be separated by conventional techniques known to those skilled in the art. See, e.g. "Stereochemistry of Organic Compounds" by E. L. Eliel (Wiley, N.Y., 1994), the disclosure of which is incorporated herein by reference in its entirety.

Where a compound of Formula I contains an alkenyl or alkenylene group, geometric cis/trans (or Z/E) isomers are possible. Cis/trans isomers may be separated by conventional techniques well known to those skilled in the art, for example, chromatography and fractional crystallization.

Salts of the present invention can be prepared according to methods known to those of skill in the art.

Polymorphs can be prepared according to techniques well-known to those skilled in the art.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of formula I contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, Stereochemistry of Organic Compounds by E. L. Eliel and S. H. Wilen (Wiley, 1994).

The invention also includes isotopically-labeled compounds of Formula I, wherein one or more atoms is replaced by an atom having the same atomic number, but an atomic mass or mass number different from the atomic mass or mass number usually found in nature. Isotopically-labeled compounds of Formula I can generally be prepared by conventional techniques known to those skilled in the art or by processes analogous to those described herein, using an appropriate isotopically-labeled reagent in place of the non-labeled reagent otherwise employed.

The compounds of formula I should be assessed for their biopharmaceutical properties, such as solubility and solution stability (across pH), permeability, etc., in order to select the most appropriate dosage form and route of administration for treatment of the proposed indication.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in Remington's Pharmaceutical Sciences, 19th Edition (Mack Publishing Company, 1995).

The compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula I, a film-forming polymer, a binder, a solvent, a humectant, a plasticiser, a stabiliser or emulsifier, a viscosity-modifying agent and a solvent. Some components of the formulation may perform more than one function.

The compound of formula I may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula I may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula I used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic)acid (PGLA) microspheres.

The compounds of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3, 3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula I, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, gels, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I a prodrug thereof or a salt of such compound or prodrug and a second compound as described above. The kit comprises means for containing the separate compositions such as a container, a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, etc. . . . Second Week, Monday, Tuesday, . . . " etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

All publications, including but not limited to, issued patents, patent applications, and journal articles, cited in this application are each herein incorporated by reference in their entirety.

Although the invention has been described above with reference to the disclosed embodiments, those skilled in the art will readily appreciate that the specific experiments detailed below are only illustrative of the invention. It should be understood that various modifications can be made without departing from the spirit of the invention. Accordingly, the invention is limited only by the claims.

Examples

Synthesis of N-(3,5-diimino-2-methyl-7-thia-2,4,6-triazanonan-9-yl)acetamide 1a

Step 2

Synthesis of N-(2-((1,3-dioxoisoindolin-2-yl)thio)ethyl)acetamide IIa

The bis acetate cystamine IVa (1.13 g, 5.0 mmol) and phthalimide (1.41 g, 10 mmol, 2.0 eq) were dissolved in acetonitrile (47 mL). To this solution, was added bromine (300 μl, 6.0 mmol, 1.2 eq) followed by pyridine (1.16 mL, 14 mmol, 3.0 eq) and the reaction mixture was stirred at room temperature for 12 h. The solvent was evaporated to give the crude material which was purified by flash silica gel chromatography (ISCO, 40 g silica gel, $CH_2Cl_2$: MeOH 0% to 15% MeOH) to give the desired product IIa as white solid (yield: 85%).

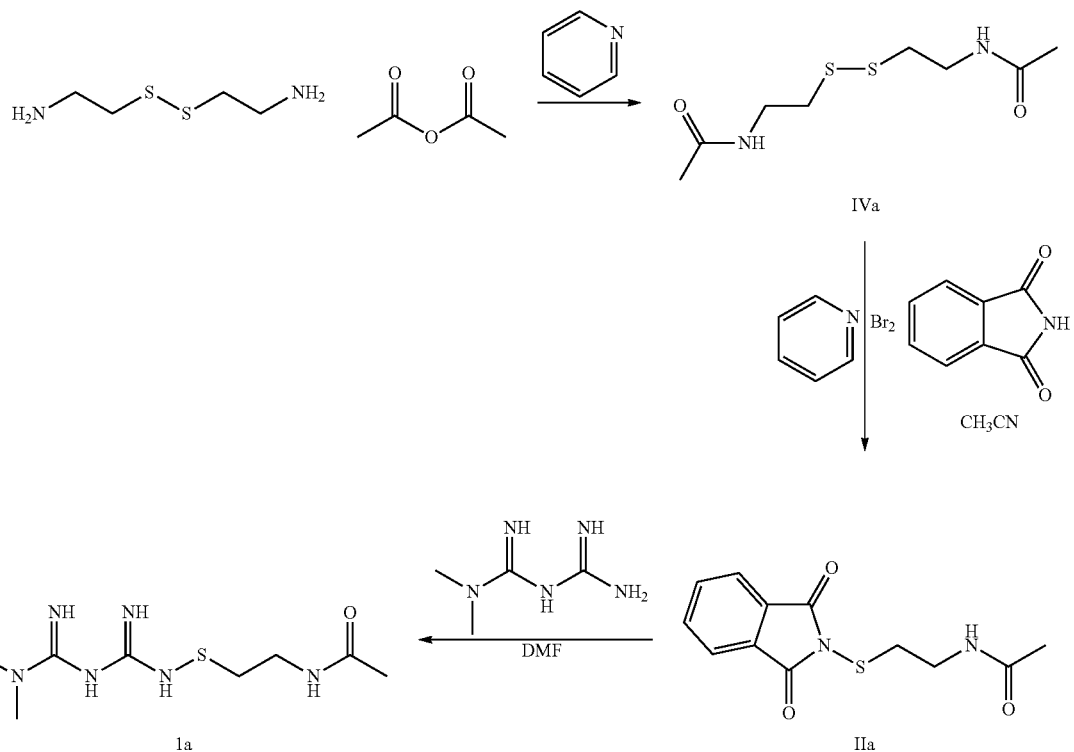

Step 1

Synthesis of N,N'-(disulfanediylbis(ethane-2,1-diyl))diacetamide IVa

Cystamine dihydrochloride (2.0 g, 8.88 mmol) was suspended in pyridine (6 mL). To this was added acetic anhydride (5.03 mL, 53.2 mmol, 6 eq) and the reaction mixture was stirred for 4 h until all solids dissolved. Pyridine was evaporated under vacuum and the crude material was purified by flash silica gel chromatography (ISCO, 40 g silica gel, $CH_2Cl_2$: MeOH 0% to 15% MeOH) to give the desired product as a white solid (yield: 80%).

Step 3

Synthesis of N-(3,5-diimino-2-methyl-7-thia-2,4,6-triazanonan-9-yl)acetamide 1a

To a solution of free base metformin (100 mg, 0.774 mmol) in DMF (7.7 mL) was added the cystamine-phthalimide IIa (204.6 mg, 0.774 mmol, 1.0 eq). The reaction mixture was stirred at room temperature for 2 h after which the solvent was evaporated. The resulting crude material was purified by flash gel chromatography (ISCO, 12 g, silica gel, $CH_2Cl_2$: MeOH 0% to 30% MeOH) to give the desired product 1a containing 20% metformin. it's very difficult to purify the desired product from metformin using normal and reverse phase chromatography.

Synthesis of 3,5-diimino-2,17,17-trimethyl-11,15-dioxo-7-thia-2,4,6,10,14-pentaazaoctadecane-16,18-diyl diacetate 1b

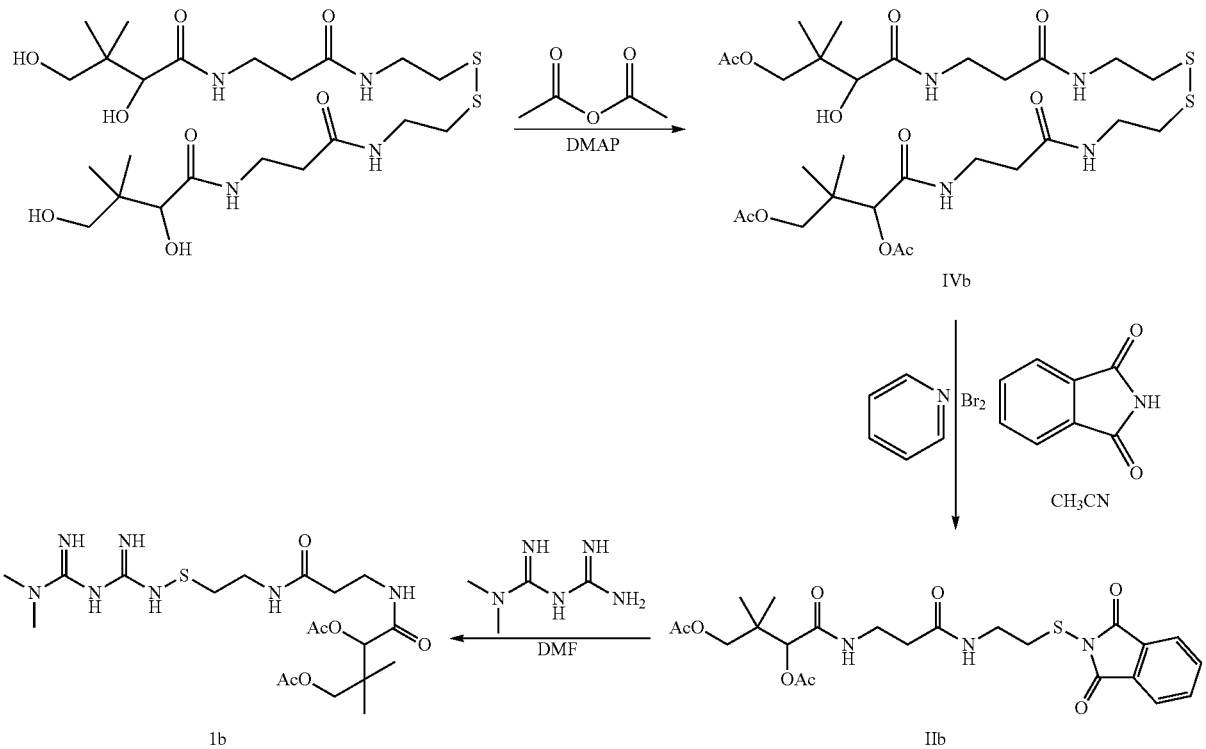

Step 1

Synthesis of 3,22-diacetoxy-2,2,23,23-tetramethyl-4,8,17,21-tetraoxo-12,13-dithia-5,9,16,20-tetraaza-tetracosane-1,24-diyl diacetate IVb To a suspension of D-pantethine (500 mg, 0.901 mmol) in acetic anhydride (9 mL) was added DMAP (5.51 mg, 0.045 mmol, 0.05 eq). The reaction mixture was stirred at room temperature for 12 h then the solvent was evaporated under vacuum. The crude material was dissolved in EtOAc and washed with $NH_4Cl$ saturated solution followed by water, brine, dried over Na2SO4, filtered and the solvent was evaporated to give the desired product IVb as white solid (yield 90%). ($^1$H NMR ($CDCl_3$): 0.99 (s, 6H), 1.01 (s, 6H), 2.03 (s, 6H), 2.39 (t, 2H), 2.76 (t, 2H), 2.92 (s, 6H), 3.30-3.62 (m, 6H), 3.88 (s, 1H)

Step 2

Synthesis of 4-((3-((2-((1,3-dioxoisoindolin-2-yl)thio)ethyl)amino)-3-oxopropyl)amino)-2,2-dimethyl-4-oxobutane-1,3-diyl diacetate IIb The 3,22-diacetoxy-2,2,23,23-tetramethyl-4,8,17,21-tetraoxo-12,13-dithia-5,9,16,20-tetraazatetracosane-1,24-diyl diacetate IVb (548 mg, 0.758 mmol) and phthalimide (223 mg, 1.51 mmol, 2.0 eq) were dissolved in acetonitrile (8 mL). To this solution, was added bromine (47 μl, 0.91 mmol, 1.2 eq) followed by pyridine (184 μl, 2.27 mmol, 3.0 eq) and the reaction mixture was stirred at room temperature for 12 h. The solvent was evaporated to give the crude material which was purified by flash silica gel chromatography (ISCO, 40 g silica gel, $CH_2Cl_2$: MeOH 0% to 15% MeOH) to give the desired product IIb (Yield 100% (containing 20% phthalimide)).

Step 3

Synthesis of 3,5-diimino-2,17,17-trimethyl-11,15-dioxo-7-thia-2,4,6,10,14-pentaazaoctadecane-16,18-diyl diacetate 1b To a solution of free base metformin (143 mg, 1.11 mmol) in DMF (11 mL) was added the 4-((3-((2-((1,3-dioxoisoindolin-2-yl)thio)ethyl)amino)-3-oxopropyl)amino)-2,2-dimethyl-4-oxobutane-1,3-diyl diacetate IIb (565 mg, 1.11 mmol, 1.0 eq). The reaction mixture was stirred at room temperature for 2 h after which the solvent was evaporated. The resulting crude material was purified by flash gel chromatography (ISCO, 12 g, silica gel, $CH_2Cl_2$:MeOH 0% to 30% MeOH) to give the desired product. The resulting oil was crystallised with $CH_2Cl_2$:Hex (mixture 1:1), then the solvent was evaporated to give the desire product Ib as white solid (Yield 15%). $^1$H NMR (200 MHz, $D_2O$): δ3.92 (d, 1H), 3.72 (d, 1H), 3.60-3.22 (m, 4H), 3.20 (s, 1H), 2.91 (s, 6H), 2.71 (t, 2H), 2.37 (t, 2H), 2.05 (s, 3H), 1.95 (s, 3H), 0.88 (d, 6H).

Synthesis of N-(3,5-diimino-2-methyl-11-oxo-7-thia-2,4,6,10-tetraazatridecan-13-yl)-2,4-dihydroxy-3,3-dimethylbutanamide 1c

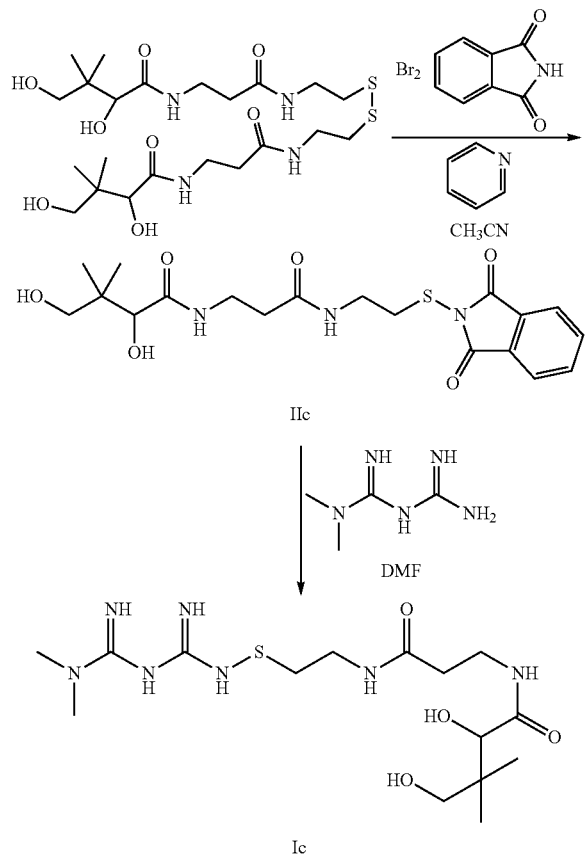

Step 1

Synthesis of N-(3-((2-((1,3-dioxoisoindolin-2-yl)thio)ethyl)amino)-3-oxopropyl)-2,4-dihydroxy-3,3-dimethylbutanamide IIc The D-pantethine (1000 mg, 1.81 mmol) and phthalimide (530 mg, 3.61 mmol, 2.0 eq) were dissolved in acetonitrile (18 mL). To this solution, was added bromine (111 μl, 2.16 mmol, 1.2 eq) followed by pyridine (435 μl, 5.41 mmol, 3.0 eq) and the reaction mixture was stirred at room temperature for 12 h. The solvent was evaporated to give the crude material which was purified by flash silica gel chromatography (ISCO, 40 g silica gel, $CH_2Cl_2$:MeOH 0% to 15% MeOH) to give the desired product IIc as red solid (Yield over 100% (containing 30% of phthalimide). ($^1$H NMR ($CD_3OD$): 0.91 (s, 6H), 0.81 (s, 3H), 2.43 (t, 2H), 2.84 (t, 2H), 3.30-3.70 (m, 5H), 3.90 (s, 1H), 8.19 (m, 2H), 8.70 (m, 1H), 8.95 (m, 2H).

Step 2

Synthesis of N-(3,5-diimino-2-methyl-11-oxo-7-thia-2,4,6,10-tetraazatridecan-13-yl)-2,4-dihydroxy-3,3-dimethylbutanamide 1c To a solution of free base metformin (255 mg, 1.98 mmo, 1.1 eq) in DMF (18 mL) was added the N-(3-((2-((1,3-dioxoisoindolin-2-yl)thio)ethyl)amino)-3-oxopropyl)-2,4-dihydroxy-3,3-dimethylbutanamide IIc (762 mg, 1.80 mmol, 1.0 eq). The reaction mixture was stirred at room temperature for 2 h after which the solvent was evaporated. The resulting crude material was purified by flash gel chromatography (ISCO, 12 g, silica gel, $CH_2Cl_2$:MeOH 0% to 30% MeOH) to give the desired product Ic (Yield 82% as a white solid). $^1$H NMR (200 MHz, $D_2O$): δ3.84 (s, 1H), 3.42-3.38 (m, 5H), 3.25 (d, 1H), 2.91 (s, 6H), 2.72 (t, 2H), 2.38 (t, 2H), 0.88 (d, 6H).

Biological Assays and Data

Methods for determining the activity of the compounds of the invention are well known to those skilled in the art. One measure of interest relates to activation of AMP-activated protein kinase (AMPK). Such activity may be determined according to methods analogous to those described in Kim Y D, Park K G, Lee Y S, et al. Metformin inhibits hepatic gluconeogenesis through AMP-activated protein kinase-dependent regulation of the orphan nuclear receptor SHP. Diabetes. 2008; 57(2):306-14. Other methods for determining the activity and pharmacokinetics of the compounds of the invention are described in Efficacy, Tolerability, and Safety of a Novel Once-Daily Extended-Release Metformin in Patients With Type 2 Diabetes, Schwartz et al., Diabetes Care, 29, 4, 759-764 (2006); and Population Exposure-Response Modeling of Metformin in Patients With Type 2 Diabetes Mellitis, Ying Hong, Shashank Rohatagi, Bahru Habtemariam, Joseph R. Walker, Sherwyn L. Schwartz and Donald E. Mager, J. Clin. Pharmacol., 48: 696 (2008).

The invention claimed is:

1. A compound of the Formula

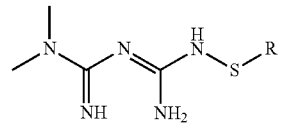

wherein R is

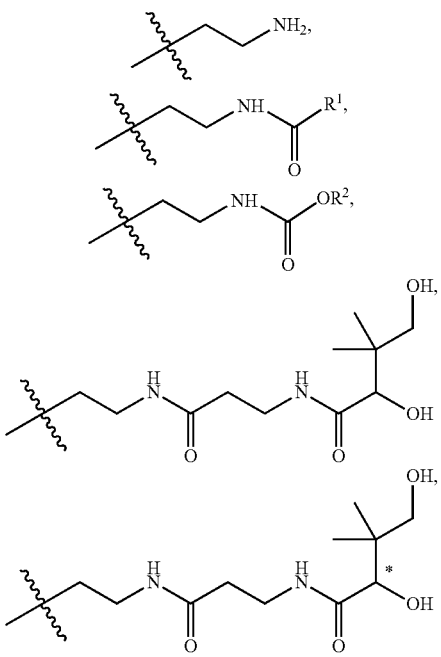

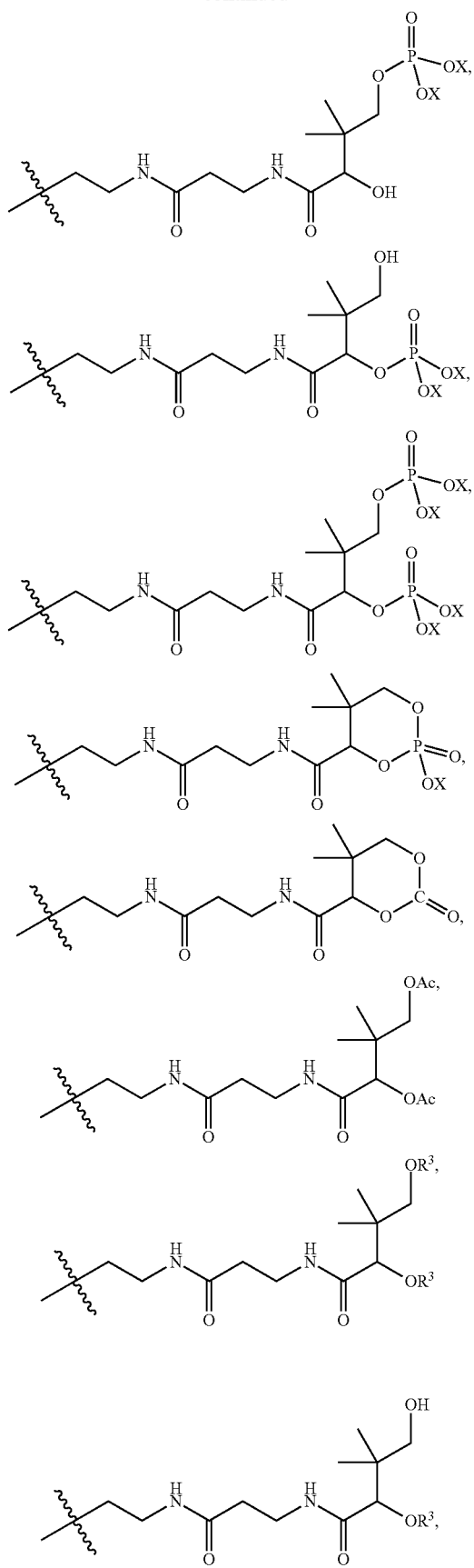

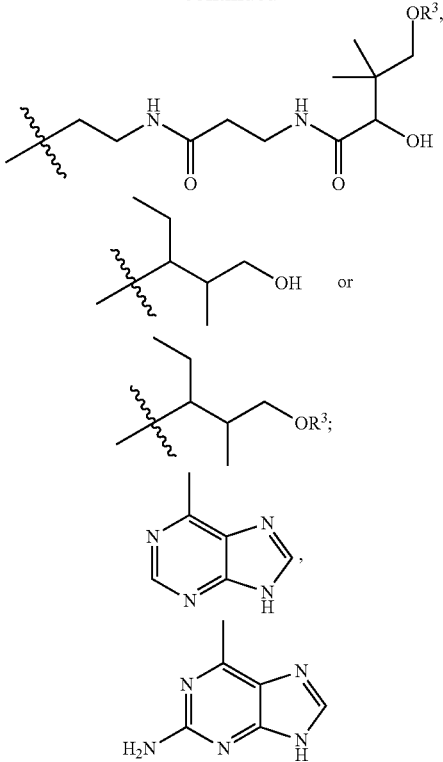

R[1] is alkyl, functionalized (heteroatom substituted) alkyl, cycloalkyl, aryl, heteroaryl, heterocyclic, carboxylate drug conjugate, fatty acid conjugate, bile acid conjugate, or amino acid conjugate;

R[2] is alkyl, cycloalkyl, heterocyclic, aryl

R[3] is (C=O)R[2], C(R[4])$_2$O(C=O)R[5], C(R[4])$_2$O(C=O)OR[5], C(R[4])$_2$O(P=O)(OX)$_2$, C(R[4])$_2$O(C=O)N(R[6])$_2$, C(R[4])$_2$O(C=O)(CHR[4])NR[6]R[4], or C(R[4])$_2$O(C=O)(CHR[6])N(R[6])$_2$,

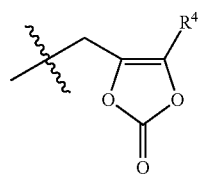

R[4] is H, alkyl, cycloalkyl, CO$_2$R[1]

R[5] is alkyl, functionalized alkyl, cycloalkyl, aryl, or heteroaryl;

R[6] is H or R[5]; and

X is H, Na$^+$, K$^+$, Ca$^{2+}$, Mg$^{2+}$, $^+$NH$_3$CH$_2$CH$_2$OH, $^+$N(R[2])$_4$, $^+$NH$_4$.

2. A compound according to claim 1 wherein R is

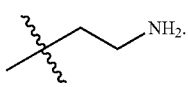 [SMILES: *CCN]

3. A compound according to claim 1 wherein R is

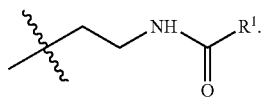

4. A compound according to claim 1 wherein R is

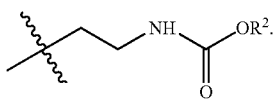

5. A compound according to claim 1 wherein R is

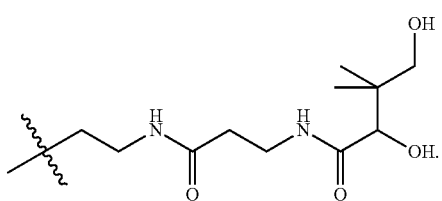 [SMILES: *CCNC(=O)CCNC(=O)C(O)C(C)(C)CO]

6. A compound according to claim 1 wherein R is

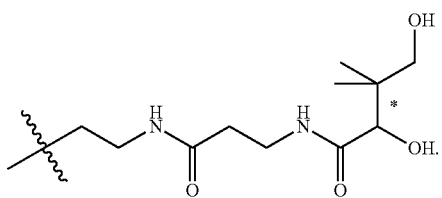 [SMILES: *CCNC(=O)CCNC(=O)C(O)C(C)(C)CO]

7. A compound according to claim 1 wherein R is

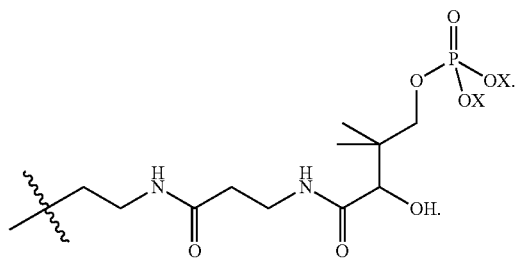

8. A compound according to claim 1 wherein R is

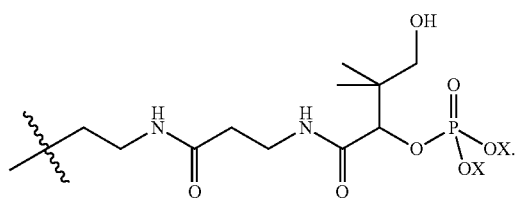

9. A compound according to claim 1 wherein R is

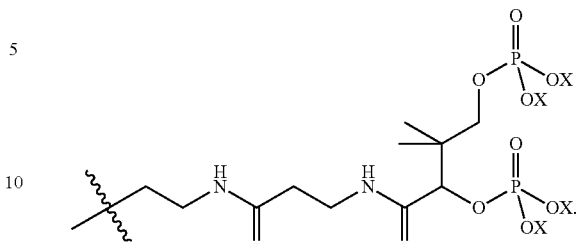

10. A compound according to claim 1 wherein R is

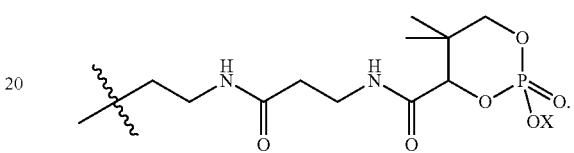

11. A compound according to claim 1 wherein R is

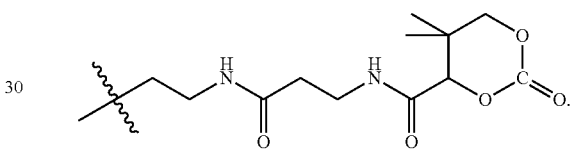

12. A compound according to claim 1 wherein R is

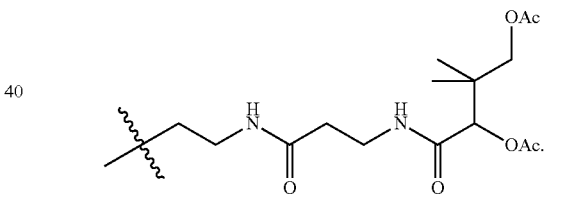

13. A compound according to claim 1 wherein R is

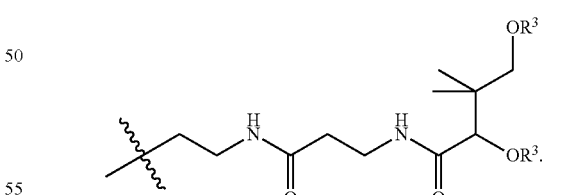

14. A compound according to claim 1 wherein R is

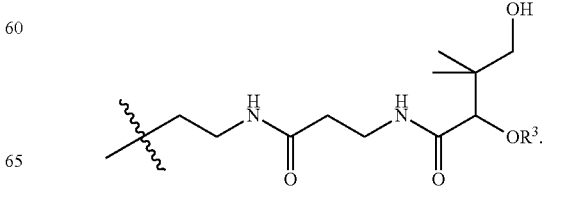

15. A compound according to claim 1 wherein R is

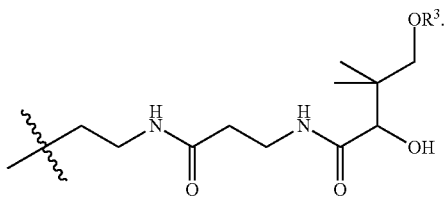

16. A compound according to claim 1 wherein R is

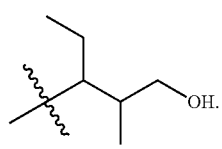 [SMILES: *C(CC)C(C)CO]

17. A compound according to claim 1 wherein R is

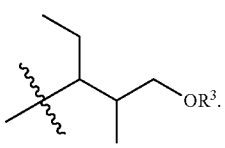

18. A pharmaceutical composition comprising a compound according to claim 1, and a pharmaceutically acceptable carrier.

19. A method for the treatment of diabetes in a mammal in need of such treatment comprising administering to said mammal a therapeutically effective amount of a compound of Formula I as defined in claim 1.

* * * * *